(12) United States Patent
Sawetzki et al.

(10) Patent No.: US 9,885,644 B2
(45) Date of Patent: Feb. 6, 2018

(54) DYNAMIC VISCOELASTICITY AS A RAPID SINGLE-CELL BIOMARKER

(71) Applicant: Colorado School of Mines, Golden, CO (US)

(72) Inventors: Tobias Sawetzki, Lakewood, CO (US); David W. M. Marr, Golden, CO (US); Charles Eggleton, Chevy Chase, MD (US); Sanjay Desai, Golden, CO (US)

(73) Assignees: Colorado School of Mines, Golden, CO (US); National Institute of Health, Bethesda, MD (US); University of Maryland, Baltimore, MD (US)

( * ) Notice: Subject to any disclaimer, the term of this patent is extended or adjusted under 35 U.S.C. 154(b) by 0 days.

(21) Appl. No.: 14/307,269

(22) Filed: Jun. 17, 2014

(65) Prior Publication Data

US 2014/0366638 A1    Dec. 18, 2014

Related U.S. Application Data

(60) Provisional application No. 61/835,971, filed on Jun. 17, 2013.

(51) Int. Cl.
*G01N 3/02* (2006.01)
*G02B 21/32* (2006.01)
*B01L 3/00* (2006.01)

(52) U.S. Cl.
CPC ............... *G01N 3/02* (2013.01); *G02B 21/32* (2013.01); *B01L 3/502761* (2013.01); *G01N 2203/0089* (2013.01)

(58) Field of Classification Search
CPC .... G01N 33/4833; G01N 3/02; G01N 33/574; G01N 2015/1495; G01N 2015/1006; H05H 3/04; G02B 21/32

USPC .......................................................... 73/788
See application file for complete search history.

(56) References Cited

U.S. PATENT DOCUMENTS

| | | |
|---|---|---|
| 4,190,535 A | 2/1980 | Luderer |
| 5,002,647 A | 3/1991 | Tanabe et al. |
| 5,021,224 A | 6/1991 | Nakajima |
| 5,098,850 A | 3/1992 | Nishida et al. |
| 5,148,511 A | 9/1992 | Savu et al. |
| 5,176,786 A | 1/1993 | Debe |

(Continued)

FOREIGN PATENT DOCUMENTS

| | | |
|---|---|---|
| DE | 19712309 | 5/1998 |
| EP | 1221342 | 7/2002 |

(Continued)

OTHER PUBLICATIONS

Official Action for U.S. Appl. No. 12/239,449, dated Jan. 2, 2015 9 pages.

(Continued)

*Primary Examiner* — Harshad R Patel
*Assistant Examiner* — Brandi Hopkins
(74) *Attorney, Agent, or Firm* — Sheridan Ross P.C.

(57) ABSTRACT

The present invention generally relates to a method for determining the dynamic viscoelastic properties of cells, more particularly to a method for rapidly determining the dynamic viscoelastic properties of healthy and unhealthy cells by determining the phase shift be the application of a modulating force to the cells and the cells' response to the modulating force.

20 Claims, 10 Drawing Sheets

(56) References Cited

U.S. PATENT DOCUMENTS

| | | |
|---|---|---|
| 5,187,089 A | 2/1993 | Scott et al. |
| 5,304,487 A | 4/1994 | Wilding et al. |
| 5,427,663 A | 6/1995 | Austin |
| 5,512,745 A | 4/1996 | Finer et al. |
| 5,541,072 A | 7/1996 | Wang et al. |
| 5,622,831 A | 4/1997 | Liberti et al. |
| 5,639,669 A | 6/1997 | Ledley |
| 5,707,799 A | 1/1998 | Hansmann et al. |
| 5,715,946 A | 2/1998 | Reichenbach |
| 5,750,339 A | 5/1998 | Smith |
| 5,753,038 A | 5/1998 | Vichr et al. |
| 5,770,029 A | 6/1998 | Nelson et al. |
| 5,837,115 A | 11/1998 | Austin |
| 5,855,753 A | 1/1999 | Trau et al. |
| 5,858,188 A | 1/1999 | Soane et al. |
| 5,866,345 A | 2/1999 | Wilding et al. |
| 5,928,880 A | 7/1999 | Wilding et al. |
| 5,952,173 A | 9/1999 | Hansmann et al. |
| 6,007,690 A | 12/1999 | Nelson |
| 6,017,390 A | 1/2000 | Charych et al. |
| 6,054,034 A | 4/2000 | Soane et al. |
| 6,055,106 A | 4/2000 | Grier et al. |
| 6,067,859 A * | 5/2000 | Kas .................. G21K 1/006 250/251 |
| 6,074,827 A | 6/2000 | Nelson |
| 6,128,006 A | 10/2000 | Rosenberg et al. |
| 6,156,270 A | 12/2000 | Buechler |
| 6,187,089 B1 | 2/2001 | Phillips et al. |
| 6,197,523 B1 | 3/2001 | Rimm et al. |
| 6,221,671 B1 | 4/2001 | Groner et al. |
| 6,241,894 B1 | 6/2001 | Briggs et al. |
| 6,251,691 B1 | 6/2001 | Seul |
| 6,256,093 B1 | 7/2001 | Ravid et al. |
| 6,256,096 B1 | 7/2001 | Johnson |
| 6,265,229 B1 | 7/2001 | Fodstad et al. |
| 6,315,940 B1 | 11/2001 | Nisch et al. |
| 6,344,326 B1 | 2/2002 | Nelson |
| 6,361,958 B1 | 3/2002 | Shieh |
| 6,368,871 B1 | 4/2002 | Christel et al. |
| 6,387,290 B1 | 5/2002 | Brody et al. |
| 6,406,903 B2 | 6/2002 | Bray et al. |
| 6,432,630 B1 | 8/2002 | Blankenstein |
| 6,454,938 B2 | 9/2002 | Moon et al. |
| 6,465,225 B1 | 10/2002 | Fuhr et al. |
| 6,468,346 B2 | 10/2002 | Arnowitz et al. |
| 6,533,903 B2 | 3/2003 | Hayward et al. |
| 6,540,895 B1 | 4/2003 | Spence et al. |
| 6,565,225 B2 | 5/2003 | Mabuchi et al. |
| 6,613,525 B2 | 9/2003 | Nelson et al. |
| 6,632,619 B1 | 10/2003 | Harrison et al. |
| 6,635,163 B1 | 10/2003 | Han et al. |
| 6,664,104 B2 | 12/2003 | Pourahmadi et al. |
| 6,685,841 B2 | 2/2004 | Lopez et al. |
| 6,744,038 B2 | 6/2004 | Wang et al. |
| 6,746,503 B1 | 6/2004 | Benett et al. |
| 6,762,059 B2 | 7/2004 | Chan et al. |
| 6,783,647 B2 | 8/2004 | Culbertson et al. |
| 6,784,420 B2 | 8/2004 | Wang et al. |
| 6,797,057 B1 | 9/2004 | Amos et al. |
| 6,802,489 B2 | 10/2004 | Marr et al. |
| 6,815,664 B2 | 11/2004 | Wang et al. |
| 6,830,936 B2 | 12/2004 | Anderson et al. |
| 6,833,542 B2 | 12/2004 | Wang et al. |
| 6,878,271 B2 | 4/2005 | Gilbert et al. |
| 6,881,315 B2 | 4/2005 | Iida et al. |
| 6,893,502 B2 | 5/2005 | Papadimitrakopoulos et al. |
| 6,893,881 B1 | 5/2005 | Fodstad et al. |
| 6,913,697 B2 | 7/2005 | Lopez et al. |
| 6,958,245 B2 | 10/2005 | Seul et al. |
| 6,991,939 B2 | 1/2006 | Walt et al. |
| 7,068,874 B2 | 6/2006 | Wang et al. |
| 7,088,455 B1 | 8/2006 | Kirkpatrick et al. |
| 7,150,812 B2 | 12/2006 | Huang et al. |
| 7,155,082 B2 | 12/2006 | Oakey et al. |
| 7,202,045 B2 | 4/2007 | Hanash et al. |
| 7,205,157 B2 | 4/2007 | Jurgensen et al. |
| 7,214,298 B2 | 5/2007 | Spence et al. |
| 7,214,348 B2 | 5/2007 | Desmond et al. |
| 7,241,988 B2 | 7/2007 | Gruber et al. |
| 7,276,170 B2 | 10/2007 | Oakey et al. |
| 7,294,503 B2 | 11/2007 | Quake et al. |
| 7,312,085 B2 | 12/2007 | Chou et al. |
| 7,318,902 B2 | 1/2008 | Oakey et al. |
| 7,435,568 B2 | 10/2008 | Kas et al. |
| 7,442,339 B2 | 10/2008 | Sundararajan et al. |
| 7,460,240 B2 * | 12/2008 | Akcakir .................. B82Y 20/00 356/457 |
| 7,472,794 B2 | 1/2009 | Oakey et al. |
| 7,638,339 B2 | 12/2009 | Sundararajan et al. |
| 7,651,838 B2 | 1/2010 | Paterlini-Brechot |
| 7,713,705 B2 | 5/2010 | Buechler et al. |
| 7,745,788 B2 | 6/2010 | Appleyard et al. |
| 2002/0062783 A1 | 5/2002 | Bray |
| 2002/0108859 A1 | 8/2002 | Wang et al. |
| 2002/0113204 A1 | 8/2002 | Wang et al. |
| 2002/0115163 A1 | 8/2002 | Wang et al. |
| 2002/0123112 A1 | 9/2002 | Wang et al. |
| 2002/0172987 A1 | 11/2002 | Terstappen et al. |
| 2003/0024470 A1 | 2/2003 | Myerson |
| 2003/0072682 A1 | 4/2003 | Kikinis |
| 2003/0124516 A1 | 7/2003 | Chung et al. |
| 2004/0067167 A1 * | 4/2004 | Zhang .................. G01N 15/147 422/82.05 |
| 2005/0175478 A1 | 8/2005 | Marr et al. |
| 2006/0060767 A1 | 3/2006 | Wang et al. |
| 2006/0142632 A1 | 6/2006 | Meretei |
| 2006/0171846 A1 | 8/2006 | Marr et al. |
| 2007/0125941 A1 | 6/2007 | Lee et al. |
| 2008/0093306 A1 | 4/2008 | Oakey et al. |
| 2009/0026387 A1 | 1/2009 | Squier et al. |
| 2009/0062828 A1 | 3/2009 | Marr |
| 2009/0110010 A1 | 4/2009 | Squier et al. |
| 2009/0188795 A1 | 7/2009 | Oakey et al. |
| 2009/0280518 A1 * | 11/2009 | Adamo .................. G01N 33/48728 435/29 |
| 2013/0183660 A1 | 7/2013 | Yu et al. |
| 2013/0230879 A1 | 9/2013 | Neeves et al. |

FOREIGN PATENT DOCUMENTS

| | | |
|---|---|---|
| EP | 1412729 | 1/2003 |
| EP | 1438398 | 5/2003 |
| EP | 1338894 | 8/2003 |
| EP | 1485713 | 9/2003 |
| EP | 1499706 | 10/2003 |
| EP | 1539350 | 1/2004 |
| EP | 1529211 | 2/2004 |
| EP | 1542802 | 3/2004 |
| EP | 1418003 | 5/2004 |
| EP | 1462800 | 9/2004 |
| EP | 919812 | 10/2004 |
| WO | WO 94/29707 | 12/1994 |
| WO | WO 98/10267 | 3/1998 |
| WO | WO 99/44064 | 9/1999 |
| WO | WO 00/00816 | 1/2000 |
| WO | WO 02/12896 | 2/2002 |
| WO | WO 02/28523 | 4/2002 |
| WO | WO 02/30562 | 4/2002 |
| WO | WO 02/44689 | 6/2002 |
| WO | WO 03/031938 | 4/2003 |
| WO | WO 03/066191 | 8/2003 |
| WO | WO 2004/029221 | 4/2004 |
| WO | WO 2004/037374 | 5/2004 |
| WO | WO 2004/056978 | 7/2004 |

OTHER PUBLICATIONS

Applegate et al., "Microfluidic sorting system based on optical waveguide integration and diode laser bar trapping", Lab on a Chip, Jan. 20, 2006, vol. 6, pp. 422-426, The Royal Society of Chemistry.
Applegate et al., "Optical trapping, manipulation, and sorting of cells and colloids in microfluidic systems with diode laser bars", Colorado School of Mines, 2002, pp. 1-9.

(56) References Cited

OTHER PUBLICATIONS

Archer et al. "Cell Reactions to Dielectrophoretic Manipulation." Biochemical and Biophysical Research Communications. 1999;257:687-98.

Ashcroft et al., "Solid State Physics." Orlando, FL: Saunders College Publishing; 1976.

Ashkin et al. "Optical Trapping and Manipulation of Viruses and Bacteria," 1987, Science, vol. 235, pp. 1517-1520.

Author Unknown, "MicCell: Frequently Asked Questions", available at www.gesim.de, 2007, 4 pages.

Author Unknown, "The Optical Stretcher", available at http://www.uni/leipzig.de/~pwm/kas/os/os.html, cite updated on Nov. 23, 2005, 2 pages.

Baldessari et al., "Two touching spherical drops in uniaxial extensional flow: Analytic solution to the creeping flow problem," 2005, Journal of Colloid and Interface Science, vol. 289, pp. 262-270.

Bauer, "Advances in cell separation: recent developments in counterflow centrifugal elutriation and continuous flow cell separation." Journal of Chromatography.1999;722:55-69.

Becker et al. "Fabrication of Microstructures With High Aspect Ratios and Great Structural heights by Synchrotron Radiation Lithography, Galvanoforming, and Plastic Moulding (LIGA Process)." Microelectronic Engineering. 1986;4:35-56.

Becker et al. "Planar quartz chips with submicron channels for two-dimensional capillary electrophoresis applications." J. Micromech Microeng. 1998;9:24-28.

Beebe et al., "Functional Hydrogel Structures for Autonomous Flow Control Inside Microfluidic Channels", Nature, Apr. 6, 2000, pp. 588-590, 404, Nature Publishing Group (USA), a division of Macmillan Publishers Ltd., United Kingdom.

Benincasa et al. "Cell Sorting by One Gravity SPLITT Fractionation." Analytical Chemistry. 2005; 77(16):5294-5301.

Berg, "Random Walks in Biology." Princeton University Press. Princeton, NJ; 1993.

Brown et al. "Optical Waveguides Via Viscosity-Mismatched Microfluidic Flows." Department of Chemical Engineering, Colorado School of Mines. Applied Physics Letters 88, 134109 (2006).

Chan, et al., "DNA Mapping Using Microfluidic Stretching and Single-Molecule Detection of Flourescent Site-Specific Tags", Genome Research, 2004, vol. 14, pp. 1137-1146, Cold Spring Harbor Laboratory Press.

Chiu et al., "Patterned Deposition of Cells and Proteins Onto Surfaces by Using Three-Dimensional Microfluidic Systems", Proceedings of the National Academy of Sciences of the United States of America, Mar. 14, 2000, pp. 2408-2413, 97-#6, National Academy of Sciences, USA.

Chou et al., "A Microfabricated Device for Sizing and Sorting DNA Molecules", Proceedings of the National Academy of Sciences of the United States of America, Jan. 5, 1999, pp. 11-13, 96-#1, National Academy of Sciences, USA.

Chou et al., "Sorting by diffusion: An asymmetric obstacle course for continuous molecular separation." PNAS. 1999; 96(24):13762-13765.

De Kretser et al., "The Separation of Cell Populations using Monoclonal Antibodies attached to Sepharose." Tissue Antigens. 1980;16:317-325.

Delamarche et al., "Microfluidic Networks for Chemical Patterning of Substrates: Design and Application to Bioassays", Journal of the American Chemical Society, Jan. 9, 1998, pp. 500-508, 120, American Chemical Society, USA.

Delamarche et al., "Patterned Delivery of Immunoglobulins to Surfaces Using Microfluidic Networks", Science, May 2, 1997, pp. 779-781, 276, American Association for the Advancement of Science, USA.

Deshmukh et al., "Continuous Micromixer With Pulsatile Micropumps. Solid-State Sensor and Actuator Workshop." Hilton Head Island, South Carolina; Jun. 4-8, 2000:73-76.

Desprat, et al., "Creep Function of a Single Living Cell", Biophysical Journal, Mar. 2005, vol. 88, pp. 2224-2233, Biophysical Society.

Duffy et al., "Rapid Prototyping of Microfluidic Systems in Poly(dimethylsiloxane)", Anal. Chem., 70 (23) 4974-4984, 1998 (abstract only, if the examiner desires the full article please contact the attorney of record and a copy will be provided).

Eigen et al., "Sorting Single Molecules: Application to Diagnostics and Evolutionary Biotechnology", Proceedings of the National Academy of Sciences of the United States of America, Jun. 1994, pp. 5740-5747, 91, National Academy of Sciences, USA.

Evans et al., "The Bubble Spring and Channel (BSAC) Valve: An Actuated, Bi-Stable Mechanical Valve for In-Plane Fluid Control. Transducers '99." Sendai, Japan; Jun. 7-10, 1999.

Eyal et al., "Velocity-independent microfluidic flow cytometry", Electrophoresis, Aug. 2002;23(16):2653-7 (abstract only, if the examiner desires the full article please contact).

Farooqui et al. "Microfabrication of Submicron Nozzles in Silicon Nitride." Journal of Microelectromechanical Systems. 1992; 1(2):86-88.

Fiedler et al., "Dielectrophoretic Sorting of Particles and Cells in a Microsystem", Analytical Chemistry, May 1, 1998, pp. 1909-1915, 70-#9, American Chemical Society, USA.

Freemantle, "Downsizing Chemistry", Chemical & Engineering News, Feb. 22, 1999, pp. 27-39, 77-#8, American Chemical Society.

Fu et al., "A Microfabricated Flourescence-Activated Cell Sorter", Nature Biotechnology, Nov. 1999, pp. 1109-1111, 17, Nature America Inc., USA.

Fu et al., "An integrated miscrofabricated cell sorter." Analytical Chemistry. 2002;74(11):2451-2457.

Fuhr et al., "Biological Application of Microstructures", Topics in Current Chemistry, 1997, pp. 83-116, 194, Springer-Verlag, Germany.

Gambin et al. "Microfabricated Rubber Microscope Using Soft Solid Immersion Lenses." Department of Applied Physics, California Institute of Technology. Applied Physics Letters 88, 174102 (2006).

Gast, et al., "The development of integrated microfluidic systems at GeSiM", Lab on a Chip, 2003, vol. 3, pp. 6N-1 ON, The Royal Society of Chemistry.

Gast, et al., "The microscopy cell (MicCell), a versatile modular flowthrough system for cell biology, biomaterial research, and nanotechnology", Microfluid Nanofluid (2006), published on-line Jul. 27, 2005, vol. 2, pp. 21-36, Springer-Verlag.

Giddings, "Chemistry 'Eddy' Diffusion in Chromatography." Nature. 1959;184:357-358.

Giddings, "Field-Flow Fractionation: Analysis of Macromolecular, Colloidal, and Particulate Materials." Science. 1993;260:1456-1465.

Giddings, "Unified Separation Science." John Wiley & Sons, Inc. 1991; Cover Page & Table of Contents only.

Gu, et al., "A single beam near-field laser trap for optical stretching, folding and rotation of erythrocytes", Optics Express, Feb. 5, 2007, vol. 15, No. 3., pp. 1369-1375, Optical Society of America.

Guck, et al., "Optical Deformability as an Inherent Cell Marker for Testing Malignant Transformation and Metastatic Competence", Biophysical Journal, May 2005, vol. 88, pp. 3689-3698, Biophysical Society.

Guck, et al., "The Optical Stretcher: A Novel Laser Tool to Micromanipulate Cells", Biophysical Journal, Aug. 2001, vol. 81, pp. 767-784, Biophysical Society.

Han et al., "Separation of Long DNA Molecules in a Microfabricated Entropic Trap Array." Science. 2000;288: 1026-1029.

Huang et al., "A DNA prism for high-speed continuous fractionation of large DNA molecules." Nature Biotechnology. 2002;20:1048-1051.

Huang et al., "Role of Molecular Size in Ratchet Fractionation." 2002; 89(17):178301-1-178301-4.

Huang et al., "Electric Manipulation of Bioparticles and Macromoledules on Microfabricated Electrodes", Analytical Chemistry, Apr. 1, 2001, pp. 1549-1559, 73-#7, American Chemical Society, USA.

Huh et al., "Gravity-driven microhydrodynamics-based cell sorter (microHYCS) for rapid, inexpensive, and efficient cell separation and size-profiling." 2nd Annual International IEEE-EMBS Special

(56) References Cited

OTHER PUBLICATIONS

Topic Conference on Microtechnology in Medicine and Biology. Madison, Wisconsin USA; May 2-4, 2002:466-469.
Jeon et al., "Generation of Solution and Surface Gradients using Microfluidic Systems", Langmuir, 2000, pp. 8311-8316, 16-#22, American Chemical Society, USA.
Kamholz et al., "Quantitative Analysis of Molecular Interaction in a Microfluidic Channel: the T-Sensor", Analytical Chemistry, Dec. 1, 1999, pp. 5340-5347, 71-#23, American Chemical Society, USA.
Kenis et al., "Microfabrication Inside Capillaries Using Multiphase Laminar Flow Patterning", Science, Jul. 2, 1999, pp. 83-85, 285, American Association for the Advancement of Science, USA.
Kim et al. Polymer microstructures formed by moulding in capillaries. Nature. 1995;376:581-584.
Kim, et al., "Stretching and immobilization of DNA for studies of protein-DNA interactions at the single-molecule level", Nano Review, Apr. 18, 2007, Nanoscale Res Letter vol. 2, pp. 185-201, Springer.
Kumar et al. Cell Separation: A Review. Pathology. 1984;16:53-62.
Lang, et al., "Resource Letter: LBOT-1: Letter based optical tweezers", Am J Phys., Mar. 2003, vol. 71(3), pp. 201-215, National Institute of Health.
Li et al, "Transport, Manipulation, and Reaction of Biological Cells On-Chip Using Electrokinetic Effects", Analytical Chemistry, Apr. 15, 1997, pp. 1564-1568, 69-#8, American Chemical Society, USA.
Lim, et al., "Large deformation of living cells using laser traps", Acta Materialia, Apr. 19, 2004, vol. 52, Issue 7, pp. 1837-1845, Elsevier Science Ltd., (Only abstract and figures/tables provided, 6 pages).
Lincoln et al., "High-Throughput Rheological Measurements with an Optical Stretcher", Methods in Cell Biology, vol. 83, 2007, pp. 397-423 (abstract only, if the examiner desires the full article please contact the attorney of record and a copy will be provided).
Lincoln, et al., "Deformability-Based Flow Cytometry", Wiley InterScience, May 17, 2004, Cytometry Part A 59A, pp. 203-209, Wiley-Liss, Inc.
Lu, et al., "Viscoelastic properties of individual glial cells and neurons in the CNS", PNAS, Nov. 21, 2006, vol. 103, No. 47, pp. 17759-17764, The National Academy of Sciences of the USA.
Lumsdon et al. "Two-Dimensional Crystallization of Microspheres by a Coplanar AC Electric Field," 2004, Langmuir, vol. 20, pp. 2108-2116.
Martin et al., "Feeling with light for cancer", 2006, Progress in biomedical optics and imaging, vol. 7 (abstract only, if the examiner desires the full article please contact the attorney of record and a copy will be provided).
McClain et al., "Flow Cytometry of *Escherichia coli* on Microfluidic Devices", Anal. Chem., 73(21), 5334-5338, 2001 (abstracts only, if the examiner desires the full article please contact the attorney of record and a copy will be provided).
Mehrishi et al. "Electrophoresis of cells and the biological relevance of surface charge." Electrophoresis. 2002;23:1984-1994.
MicCell™ Parts List, GeSiM, www.gesim.de, 2007, 2 pages.
Moore et al. Lymphocyte fractionation using immunomagnetic colloid and a dipole magnet flow cell sorter. J Biochem Biophys Methods. 1998;37:11-33.
Oakey et al., "Laminar Flow-Based Separations at the Microscale", Biotechnology Progress, Sep. 24, 2002, pp. 1439-1442, 18-#6, American Chemical Society and the American Institute of Chemical Engineers, USA.
Pamme et al., "Counting and sizing of particles and particle agglomerates in a microfluidic device using laser light scattering: application to a particle-enhanced immunoassay", Lap Chip, 2003, 3, 187-192.
Raymond et al. "Continuous Separation of High Molecular Weight Compounds using a Microliter Volume Free-Flow Electrophoresis Microstructure." 1996;68:2515-2522.
Reed et al., "High throughput cell nanomechanics with mechanical imaging interferometry", 2008 Nanotechnology 19, 235101 (8 pages) (abstract only, if the examiner desires the full article please contact the attorney of record and a copy will be provided).
Sery et al.,"Compact laser tweezers," 2007, Proc. SPIE 6609, 15th Czech-Polish-Slovak Conference on Wave and Quantum Aspects of Contemporary Optics, 66090N, 2 pages (abstract only).
Singh, et al., "A Miniaturized Wide-Angle 2D Cytometer", Wiley InterScience, Feb. 23, 2006, Cytometry Part A 69A, pp. 307-315, International Society for Analytical Cytology.
Sraj et al. "Cell deformation cytometry using diode-bar optical stretchers," Journal of Biomedical Optics, Jul./Aug. 2010, vol. 15, No. 4, 7 pages.
Takayama et al. "Patterning Cells and Their Environments Using Multiple Laminar Fluid Flows in Capillary Netwoorks", Proceedings of the National Academy of Sciences of the United States of America, May 11, 1999, pp. 5545-5548, 96-#10, national Academy of Sciences, USA.
Takayama et al. "Subcellular Position of Small Molecules", Nature, Jun. 28, 2001, p. 1016, 411, Nature Publishing Group (USA), a division of Macmillan Publishers Ltd., United Kingdom.
Terray et al., "Microfluidic Control Using Colloidal Devices", Science vol. 296, Jun. 7, 2002, pp. 1841-1844.
Tong et al. Low Temperature Wafer Direct Bonding. Journal of Microelectromechanical Systems. 1994;3:29-35.
Turner et al. Confinement-Induced Entropic Recoil of Single DNA Molecules in a Nanofluidic Structure. Physical Review Letters. 2002;88:128103.1-128103.4.
Vezenov et al. "Integrated Fluorescent Light Source for Optofluidic Applications." Department of Chemistry and Chemical Biology, Harvard University. Applied Physics Letters 86, 041104 (2005).
Visscher, et al., "Single Beam Optical Trapping Integrated in a Confocal Microscope for Biological Applications", Cytometry , Apr. 10, 1991, vol. 12, pp. 485-491, Wiley-Liss, Inc.
Voldman et al. Holding Forces of Single-Particle Dielectrophoretic Traps. Biophysical Journal.2001;80:531-541.
Volkmuth et al. DNA electrophoresis in microlithographic arrays. Letters to Nature (1992) vol. 358; p. 600.
Weigl et al., "Microfluidic Diffusion-Based Separation and Detection", Science, Jan. 15, 1999, pp. 346-347, 283-#5400, American Association for the Advancement of Science, USA.
Wolfe et al. "Dynamic Control of Liquid-Core/Liquid-Cladding Optical Waveguides." Department of Chemistry and Chemical Biology. Harvard University. Aug. 24, 2004, vol. 101, No. 34. pp. 12434-12438.
Wuite, et al., "An Integrated Laser Trap/Flow Control Video Microscope for the Study of Single Biomolecules", Biophysical Journal, Aug. 2000, vol. 29, pp. 1155-1167, Biophysical Society.
Xu et al. Dielectrophoresis of human red cells in microchips. Electrophoresis. 1999;20:1829-1831.
Zhang et al. High-speed free-flow electrophoresis on chip. Anal Chem. 2003;75:5759-5766.
"Fiber Coupled LED Source and Accessories" http://www.wt-technology.com/LED.htm, printed May 16, 2011, 1 page.
Official Action for U.S. Appl. No. 10/838,908, dated Feb. 24, 2006.
Official Action for U.S. Appl. No. 10/838,908, dated Oct. 30, 2006.
Official Action for U.S. Appl. No. 10/838,908, dated Oct. 4, 2007.
Official Action for U.S. Appl. No. 10/838,908, dated May 1, 2008, 2007.
Official Action for U.S. Appl. No. 10/838,908, dated Mar. 4, 2009.
Notice of Allowance for U.S. Appl. No. 10/838,908, dated Dec. 1, 2009.
Official Action for U.S. Appl. No. 11/329,491, dated Mar. 23, 2009.
Official Action for U.S. Appl. No. 11/329,491, dated Jun. 16, 2009.
Official Action for U.S. Appl. No. 11/329,491, dated Jun. 3, 2010.
Official Action for U.S. Appl. No. 11/329,491, dated Feb. 2, 2011.
Official Action for U.S. Appl. No. 11/329,491, dated Jul. 19, 2011 11 pages.
Official Action for U.S. Appl. No. 11/960,457, dated Jun. 18, 2008.
Official Action for U.S. Appl. No. 11/960,457, dated Jun. 25, 2008.
Official Action for U.S. Appl. No. 12/315,183, dated Jan. 14, 2010.
Official Action for U.S. Appl. No. 12/167,136, dated Nov. 10, 2010.
Official Action for U.S. Appl. No. 12/167,136, dated May 16, 2011 8 pages.

(56) References Cited

OTHER PUBLICATIONS

Official Action for U.S. Appl. No. 12/203,744, dated Mar. 29, 2011 6 pages (Restriction Requirement).
Official Action for U.S. Appl. No. 12/203,744, dated May 10, 2011 7 pages.
Official Action for U.S. Appl. No. 12/239,449, dated Sep. 2, 2010 (Restriction Requirement).
Official Action for U.S. Appl. No. 12/239,449, dated Jan. 5, 2011.
Official Action for U.S. Appl. No. 12/239,449, dated May 18, 2011 9 pages.
Official Action for U.S. Appl. No. 12/239,449, dated May 1, 2014 8 pages.
Official Action for U.S. Appl. No. 13/770,875, dated Sep. 4, 2014, 12 pages.
Sawetzki et al., "Viscoelasticity as a Biomarker for High-Throughput Flow Cytometry", Biophyiscal Journal, 2013, vol. 105 (10), 8 pages.
Davies et al. "Optically Controlled Collisions of Biological Objects." SPIE Proceedings, Optical Investigations of Cells In Vitro and In Vivo, 15, Apr. 29, 1998, pp. 15-22.
Official Action for U.S. Appl. No. 12/203,744, dated Dec. 28, 2011 9 pages.
Official Action for U.S. Appl. No. 13/770,875, dated Apr. 20, 2015 10 pages.
Notice of Allowance for U.S. Appl. No. 13/770,875, dated Jul. 7, 2016, 12 pages.

\* cited by examiner

DYNAMIC VISCOELASTICITY AS A RAPID SINGLE-CELL BIOMARKER

CROSS REFERENCE TO RELATED APPLICATIONS

The present application claims priority to and the benefits of U.S. Provisional Patent Application Ser. No. 61/835,971, filed Jun. 17, 2013, entitled "DYNAMIC VISCOELASTICITY AS A RAPID SINGLE-CELL BIOMARKER", which is incorporated herein in its entirety by reference.

Cross reference is made to U.S. patent application Ser. No. 13/770,875 filed Feb. 19, 2013, entitled "OPTICAL ALIGNMENT DEFORMATION SPECTROSCOPY", which is incorporated herein by this reference in its entirety.

Cross reference is made to U.S. patent application Ser. No. 12/239,449 filed Sep. 26, 2008, entitled "FIBER-FOCUSED DIODE-BAR OPTICAL TRAPPING FOR MICROFLUDIC MANIPULATION", which is incorporated herein by this reference in its entirety.

Cross reference is made to U.S. patent application Ser. No. 12/167,136 filed Jul. 2, 2008, entitled "OPTICAL-BASED CELL DEFORMABILITY", now U.S. Pat. No. 8,119,976, which is incorporated herein by this reference in its entirety.

Cross reference is made to U.S. patent application Ser. No. 11/329,491 filed Jan. 10, 2006, entitled "MICROFLUIDIC SYSTEMS INCORPORATING INTEGRATED OPTICAL WAVEGUIDES", now abandoned, which is incorporated herein by this reference in its entirety.

STATEMENT REGARDING FEDERALLY SPONSORED RESEARCH OR DEVELOPMENT

This invention was supported in part with funding provided by National Science Foundation Grant No. DBI-0852868 and National Institutes of Health Grant No. 1R01 AI079347.

FIELD OF INVENTION

This disclosure relates to non-destructive methods of measuring a cell's physiological state, more particularly to non-destructive mechanical methods of measuring a cell's physiological state.

BACKGROUND OF THE INVENTION

Mechanical, electrical and optical properties of a cell can be an indication of a cell's physiological state. However, non-destructive methods for measuring such properties of one or more cells can be cumbersome.

Flow cytometers and fluorescence activated cell sorters are indispensable biomedical research and clinical instruments capable of detecting and sorting individual cells at rates significantly higher than 1000 cells/s. The use of such fluorescent labeling techniques may impair investigations where post-sorting cell viability is crucial. Moreover, the fluorescent labels utilized in such methods are considered potentially harmful to the cells.

As a result, but in an effort to retain the broad applicability of such cytometers, there has been increasing interest in label-free biomarkers that allow dependable and accurate cell classification.

SUMMARY OF THE INVENTION

These and other needs are addressed by the various embodiments and configurations of the present invention.

The mechanical properties of a living cell can be used as a biophysical marker of cell viability and health. The viscoelastic or mechanical response of a cell to an applied force can be a measure of the physiological and environmental state of the cell.

The present invention generally relates to a method for determining the dynamic viscoelastic properties of a cell, more particularly to a method for rapidly determining the dynamic viscoelastic properties of a cell. Furthermore, the dynamic viscoelastic method of the present disclosure avoids the disadvantages of bulk methods where averaging can mask small subpopulations.

The application of a force to a cell and measurement of the cell's response to the applied force typically occurs over a period of seconds. This is in contrast to light scattering and fluorescence methods, where cellular response can be determined in milli- or nano-seconds.

Viscoelastic measurement response periods of on the order of seconds are generally not suitable for high throughput, rapid analysis. However, viscoelastic measurements at frequencies greater than the frequencies of cell relaxation can provide substantial information about cell physiology, environment, or both.

Accordingly, in accordance with some aspects of the invention is a method of assessing cellular viscoelastic properties. The method includes generating a linear optical trap with a laser beam, the linear optical trap having a longitudinal optical trap axis and a transverse optical trap axis; containing within the linear optical trap one or more cells; applying a modulated force to the one or more cells; and measuring the lag between the applying of the modulated force to the one or more cells and the stretch of the one or more cells. The one or more cells have greater motion along the longitudinal optical trap axis than the transverse optical trap axis. The modulated force is applied by a modulated laser beam. Moreover, the modulated force stretches the one or more cells along the longitudinal optical trap axis.

In some embodiments of the invention, the modulated force has a frequency between about 0.1 to about 1,000 Hz. The laser beam, in some configurations, exposes the cell to no more than about 20 mW of laser power. Moreover, for frequencies of no more than about 500 Hz the modulated force is generally applied to the one or more cells for less than about 10 seconds. Furthermore, for frequencies of about 500 Hz or more, the modulated force is typically applied to the one or more cells for less than about 30 seconds.

Moreover, in some embodiments, the method includes flowing the one or more cells through the linear optical trap. The flow rate is typically between 500 to about 750 μm/s.

In some configurations, the laser beam has a power between about 350 to about 450 mW. Furthermore, the laser beam is typically an astigmatic laser beam.

In accordance with some embodiments, the one or more cells include twenty or more cells. In such instances, the modulated force is applied to the twenty or more cells and the lag between the applying of the modulated force to the twenty or more cells and the stretch of the twenty or more cells is measured.

In some embodiments, the one or more cells can be one of healthy cells, infected cells, or a mixture of healthy and infected cells. Moreover, the one or more cells can be one of healthy red blood cells, malaria infected red cells, or a mixture of healthy and malaria infected red blood cells.

In accordance with some aspects of the present invention is a method for assessing the relative health of a cell. The method includes: aligning the cell in an optical trap; applying a modulated stress to the aligned cell to strain the cell; and measuring the strain produced by the modulated stress. A modulated laser beam typically forms the optical trap. The optical trap applies the modulated stress to the aligned cell.

The measuring step includes measuring the lag between the applying of the stress and the cellular strain. Moreover, the method includes comparing the strain measured to a database of healthy and infected cellular strains to determine the relative health of the cell.

The optical trap is commonly in the form of a linear optical trap. The linear optical trap has a shape generally resembling one of a channel, a groove, a U-shape, and an invert arch. The optical trap has a longitudinal optical trap axis and a transverse optical trap axis. The transverse optical trap axis constrains cell movement more than the longitudinal optical trap axis.

In one aspect of the present invention, the modulated stress step has a frequency between about 0.1 to about 1000 Hz. Typically, the laser beam exposes the cell to no more than about 20 mW of laser power. Moreover, for frequencies of no more than about 500 Hz the modulated force is generally applied to the cell for less than about 10 seconds. Furthermore, for frequencies of about 500 Hz or more, the modulated force is typically applied to the cell for less than about 30 seconds.

In accordance with some aspects of the invention a method is provided for assessing viscoelastic properties of a red blood cell. The method generally comprises: generating a linear optical trap by imaging an astigmatic laser beam, the linear optical trap having a longitudinal optical trap axis and a transverse optical trap axis; containing within the linear optical trap the red blood cell; applying a modulated force having a frequency between about 0.1 to about 1,000 Hz to the red blood cell; and measuring the lag between the applying of the modulated force to the red blood cell and the stretch of the red blood cell. The red blood cell generally has greater motion along the longitudinal optical trap axis than the transverse optical trap axis. The laser beam applies the modulated force. In general, the modulated force stretches the red blood cell along the longitudinal optical trap axis. In some embodiments, the laser beam exposes the red blood cell to no more than about 20 mW of laser power.

As used herein, the term "a" or an entity refers to one or more of that entity. As such, the terms "a" (or "an"), one or more and at least one can be used interchangeably herein. It is also to be noted that the terms "comprising", "including", and "having" can be used interchangeably.

As used herein, at least one", one or more", and "and/or" are open-ended expressions that are both conjunctive and disjunctive in operation. For example, each of the expressions at least one of A, B and C", at least one of A, B, or C", one or more of A, B, and C", one or more of A, B, or C" and "A, B, and/or C" means A alone, B alone, C alone, A and B together, A and C together, B and C together, or A, B and C together.

These and other advantages will be apparent from the disclosure of the invention(s) contained herein.

The preceding is a simplified summary of the invention to provide an understanding of some aspects of the invention. This summary is neither an extensive nor exhaustive overview of the invention and its various embodiments. It is intended neither to identify key or critical elements of the invention nor to delineate the scope of the invention but to present selected concepts of the invention in a simplified form as an introduction to the more detailed description presented below. As will be appreciated, other embodiments of the invention are possible utilizing, alone or in combination, one or more of the features set forth above or described in detail below.

BRIEF DESCRIPTION OF THE DRAWINGS

The accompanying drawings are incorporated into and form a part of the specification to illustrate several examples of the present invention(s). These drawings, together with the description, explain the principles of the invention(s). The drawings simply illustrate preferred and alternative examples of how the invention(s) can be made and used and are not to be construed as limiting the invention(s) to only the illustrated and described examples.

Further features and advantages will become apparent from the following, more detailed, description of the various embodiments of the invention(s), as illustrated by the drawings referenced below.

DETAILED DESCRIPTION OF THE INVENTION

Viscoelastic materials, such as cells, have complex mechanical behavior. When undergoing deformation viscoelastic materials exhibit viscous and elastic properties.

When a viscoelastic material such as a cell is subjected to an external force in the form of a small oscillatory stress the resultant strain can be measured. The resultant strain is typically referred to as the dynamic modulus or complex elastic modulus $G^*$. The dynamic modulus $G^*$ has two components: a storage modulus $G'$ and a loss modulus $G''$. In the case of a cell, the storage modulus $G'$ is a measure of the oscillatory stress stored by the cell and the loss modulus $G''$ is a measure of the oscillatory stress dissipated by cell.

The dynamic modulus G* and the storage G' and loss G" moduli are related as follows:

$$G^* = G' + iG'' \quad (1)$$

When subject to external loading stress, the cell, due to its viscoelastic properties, does not instantaneously respond to the external loading stress but gradually deforms. The gradual deformation, in response to the external loading stress, is governed by the cell's stress relaxation creep properties or its viscoelastic properties.

Cellular deformation is strongly dependent on the oscillatory frequency of the applied stress. The timescale of the applied loading strongly influences the cell's response to the external loading stress, such as the degree to which the cell stretches in response to the external stress. Therefore, when investigating the mechanical properties of cells, measurements of elasticity alone may lead to ambiguous results when determined at timescales that do not allow the cell to respond to the applied stress, that is stretch in response to applied stress. For slow techniques measuring only a few cells, this is negligible and not a concern; however, high-throughput applications with rapid measurement rates must move beyond a pure elasticity-based cell classification.

Figure 1:
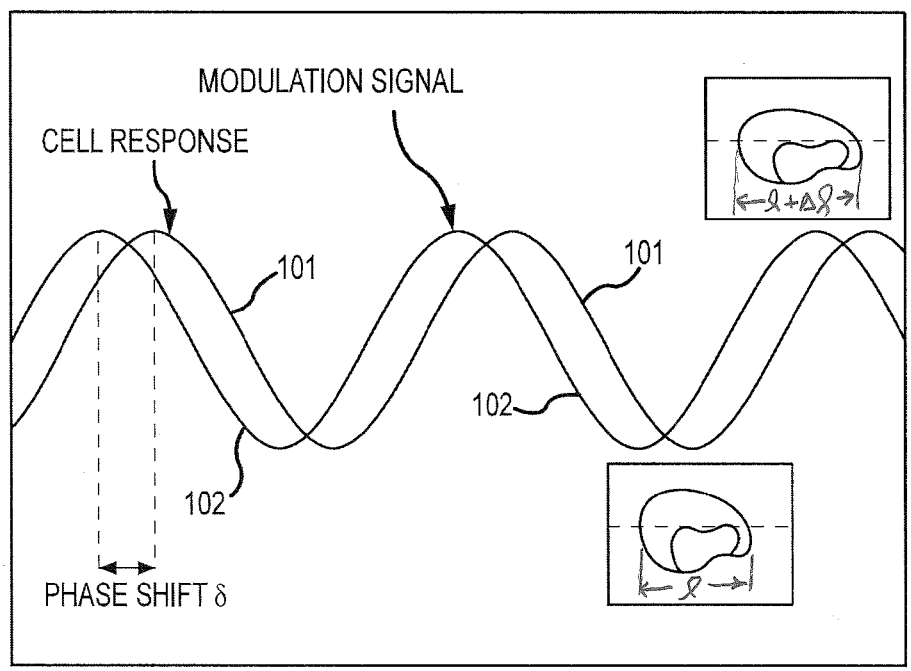
FIG. 1 depicts the time-dependent stretching behavior of a cell in response to an applied modulated force.

FIG. 1 depicts phase shift β or lag in the cellular response (strain) 101 to the applied stress or force 102.

Cellular elastic property measurement generally requires that the cell equilibrate with the externally applied force. The applied stress 102 is typically an oscillating and/or modulated loading. The modulated loading commonly has a frequency between about 0.1 to about 1,000 Hertz. The cellular relaxation time establishes an equilibrium time limitation (generally referred to as the intrinsic speed limitation). For example, red blood cells have a relaxation time of about 0.1 seconds. Stiffer cells, such as healthy white blood, breast and intestine cells can have relaxation times more than about 45 seconds.

Figure 2:
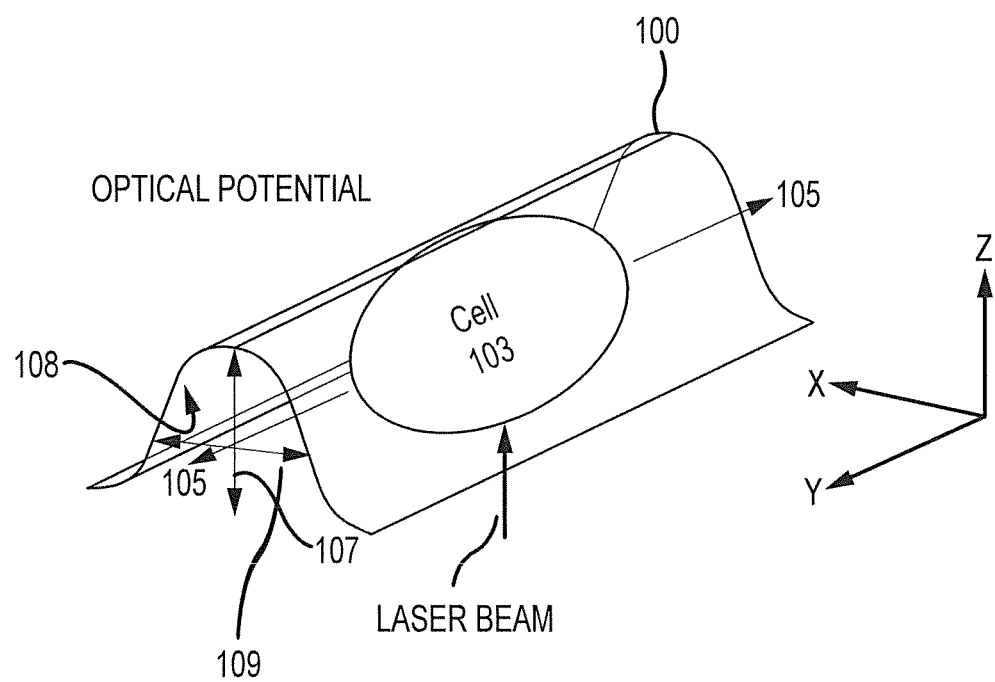
FIG. 2 depicts a cell captured in an optical trap.

Individual cells 103 can be aligned and deformed using a focused infrared laser as a sterile, non-contact optical trap 100, FIG. 2. The optical trap 100 is generally in the form of linear optical trap having a shape resembling at least one of a channel, a groove, a U-shape, and an inverted arch. The optical trap 100 has a longitudinal optical trap axis 105, a transverse optical trap axis 109, and an optical trap depth 107. The linear optical trap was created using a diode bar laser having an intrinsic astigmatism. The linear optical trap 100 allows for translational movement of the captured cell 103 along the longitudinal optical trap axis 105. However, the linear optical trap 100 constricts movement of the cell 103 along the transverse optical trap axis 109.

In general, the asymmetric distribution of laser light that forms the linear optical trap 100 applies anisotropic forces or stresses on cells constrained in the optical trap 100. The anisotropic forces induce axial, antipodal stretching forces that elongate the cell 103 along the longitudinal optical trap axis 105. After each loading, the load is released to prevent cell damage due to long-term laser radiation exposure. The distribution of relative stretching amplitudes was quantified with ΔI, the measured elongation, and l, the long axis of the cell, FIG. 1.

The anisotropic forces are due to momentum transfer from light refracted at the linear trap surface 108. The anisotropic forces are directed towards the focus center of linear optical trap, which corresponds to the longitudinal optical trap axis 105.

The anisotropic forces can be modulated and/or oscillated to determine time-dependent cellular response (strain) to the applied mechanical stress. Modulating the laser intensity modulates the anisotropic force. The laser intensity can be modulated by coupling an external frequency generator with a laser diode power source. The anisotropic can be modulated over a range from 0.05 Hz to about 1000 Hz, preferably between about 0.5 Hz to about 200 Hz.

The time-dependent viscoelastic properties of healthy and infected red cells can be determined by exposing individual cells to moderate laser powers of less than about 20 mW for 10 s at high frequencies and up to 30 s at low frequencies. The time-dependent viscoelastic properties of healthy and infected cells differed.

Figure 3:
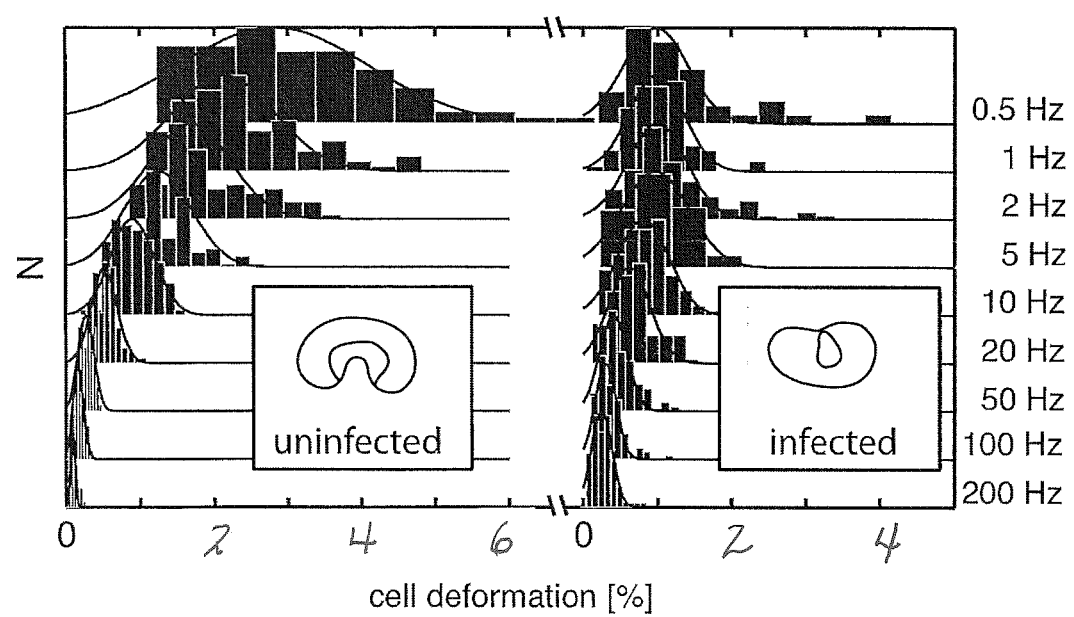
FIG. 3 depicts distributions of measured relative strains for healthy and infected cells.

FIG. 3 depicts the observed distribution of relative stretching amplitudes $\epsilon \frac{1}{4} = \Delta l/l$ of healthy and infected cells. Each distribution shows a Gaussian fit for each of measured stretching amplitudes (or relative strain), respectively, for about 100 of healthy or infected red blood cells (malaria-infected) at different applied strain modulation frequencies. A laser is typically used to generate the modulated applied force (or strain). The laser commonly has a power of no more than about 150 mW, more commonly of no more than about 125 mW, even more commonly of no more than about 100 mW, yet even more commonly of no more than about 95 mW, still yet even more commonly of no more than about 90 mW, still yet even more commonly of no more than about 85 mW, still yet even more commonly of no more than about 80 mW, still yet even more commonly of no more than about 70 mW, still yet even more commonly of no more than about 60 mW, still yet even more commonly of no more than about 50 mW, still yet even more commonly of no more than about 40 mW, still yet even more commonly of no more than about 30 mW, still yet even more commonly of no more than about 20 mW, still yet even more commonly of no more than about 10 mW, or yet still even more commonly of no more than about 5 mW.

The force is generally distributed along the entire linear optical trap 100. More generally, the force generated along the linear optical trap 100 is between about 1 to about 50 mW per cell 103 to substantially minimize, if not substantially prevent, radiation damage to cell 103. Even more generally, the force generated along the linear optical trap 100 is between about 5 to about 40 mW, yet even more generally between about 10 to about 30 mW, or still yet even more generally about 20 mW per cell 103 to substantially minimize, if not substantially prevent, radiation damage to cell 103. In some embodiments, the force generated along the linear optical trap 100 is typically no more than about 50 mW per cell 103 to substantially minimize, if not substantially prevent, radiation damage to cell 103. Even more typically, the force generated along the linear optical trap 100 is no more than about 40 mW, yet even more typically no more than about 30 mW, or still yet even more typically no more than about 20 mW per cell 103 to substantially minimize, if not substantially prevent, radiation damage to cell 103.

Figure 4:
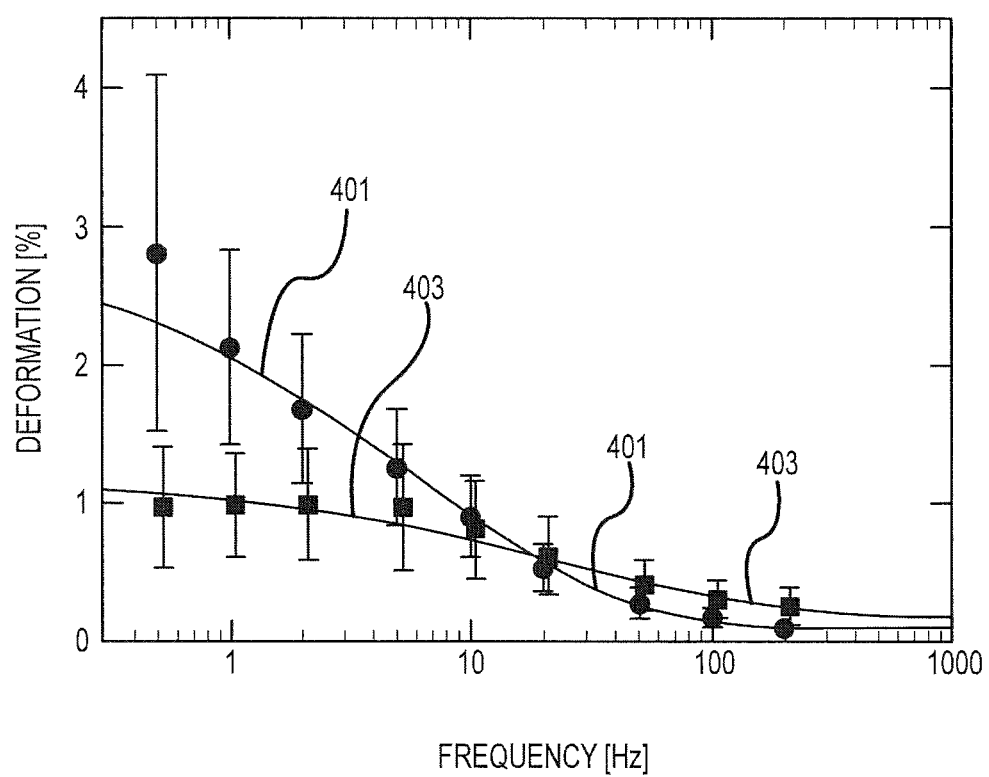
FIG. 4 depicts measured relative deformation versus applied modulation frequency for healthy and infected cells.

FIG. 4 depicts percent deformation versus applied force modulation (in Hz) for healthy cells 401 (red blood cells) and infected cells 403 (malaria-infected red blood cells). The error bars indicate one standard deviation. Distinctly reduced infected-cell deformability is observed at timescales well above relaxation times of about $\tau_R = 0.1$ s. This near-equilibrium cell stretching has a reduction in cell deformability factor of about 2.5, which agrees well with equilibrium measurements performed with other techniques such as atomic force microscopy, beadbased, and optical manipulation. However, at higher modulations of more than about 10 Hz the cells do substantially equilibrate with externally applied force and viscous creep prevents full extension and/or stretch of the cell. The deformability of the cell decreases at the higher modulation frequencies. Furthermore, the percent deformation of healthy and infected cells is substantially equivalent at modulation frequencies of more than about 10 Hz. At these short timescales, identification of infected cells based on the measured degree of stretch is less reliable. In other words, classification of a cell on elasticity alone neglects the viscoelastic nature of the cell. Moreover, neglect of a cell's viscoelastic nature limits mechanical properties analysis of cellular materials to equilibrium processes, which inherently have longer relaxation times.

The timescale for discerning viscoelastic properties of healthy and infected cells can be reduced by increasing the modulation frequency. At higher modulation frequencies cells are generally unable to equilibrate with the externally applied force and viscous creep prevents them from reaching full extension. Accordingly, the cells appear stiffer. That is, healthy and infected cells have a decreasing deformability with increasing modulation frequency. However, the measured stretch of healthy cells decays more rapidly with increasing frequency compared to infected cells. This leads to a crossover of detected deformation. Furthermore, a distinct overlap of the measured elongation of healthy and infected cell populations is generally observed at timescales approaching the cell's relaxation dynamics.

It can be appreciated that the viscoelastic property difference between healthy and infected cells is believed to be applicable not only to red blood cells but to plant and animal cells and to cells infections other than malaria. It is believed that the viscoelastic properties of cells can be affected by one or more of the following *Acanthamoeba* infection, *Acinetobacter* infection, Acquired Immune Deficiency Syndrome (AIDS), Adenovirus infection, African Trypanosomiasis infection, Alkhurma hemorrhagic fever, Amyotrophic Lateral Sclerosis, Alzheimer's Disease, *Entamoeba histolytica* infection, American Trypanosomiasis, *Angiostrongylus* Infection, Anisakiasis infection, Anthrax infection, Arenavirus Infection, Arthritis, Gout, lupus erythematosus infection, Ascariasis infection, Meningitis, Herpes, *B. cepacia*, *Babesia*, *Balamuthia mandrillaris*, *bartonella bacilliformis*, *Bartonella quintana*, *baylisascaris* infection, Schistosomiasis, *Blastocystis* infection, *Borrelia burgdorferi* infection, bovine spongiform encephalopathy, cancers, bronchiolitis, brucellosis, *Burkholderia cepacia, burkholderia mallei,* melioidosis, *clostridium difficile, c. gattii* cryptococcosis, *c. neoforman* cryptoccosis, campylobacteriosis, candidiasis, capillariasis, *klebsiella pneumonia*, Crimean-Congo hemorrhagic fever, *Trypanosoma cruzi* infection, Chapare Hemorrhagic Fever, Varicella disease, Chikungunya fever, *Chlamydia trachomatis* disease, *Vibrio cholera* infection, Creutzfeldt-Jakob disease, *Clonorchis* infection, *clostridium perfringens* infection, Tetanus disease, cytomegalovirus infection, Valley Fever, Diphtheria, Q Fever, *Klebsiella pneumonia*, Cronobacter infection, Cysticercosis, Dengue Fever, Dientamoebafragilis, Diphtheria, Ebola Hemorrhagic Fever, Ehrlichiosis, *Fasciola* Infection, Fibromyalgia, Tularemia, Mycotic diseases, Fungal Keratitis, Giardiasis, Gnathostomiasis, *Haemophilus*, Hansen's Disease, Hantavirus Pulmonary Syndrome, hemochromatosis, hemophilia, Hepatitis, herpes, Shingles, Heterophyiasis, Hib Infection, Histoplasmosis, Parainfluenza, Hantavirus, Papillomarius infections and cancers, Epstein-Barr Infections, Isosporiasis, Lassa Fever, Legionellosis, Listeriosis, Hepatitis, Loiasis, Lujo Hemorrrhagic Fever, Lupus, lymphatic filariasis, Molluscum contagisum, monkeypox, mucormycosis, *mycobacterium abscessus* infection, tuberculosis, *mycoplasma* pneumonia infection, myiasis, *naegleria* infection, gonerrhea, nocardiosis, norovirus infection, omsk hemorrhagic fever, onchocerciasis, *opisthorchis* infection, oropharyngeal candidiasis, paragonimiasis, *pneumocystis* pneumonia, pertussis, *yersinia pestis* infection, pneumoccal disease, prion disease, *rickettsia rickettsii* infection, *rubella*, ryptococcosis, *salmonella typhi* infection, *salmonella* infection, sappinia infection, severe acute respiratory syndrome, scarlet fever, schistosomiasis, shigellosis, sickle cell disease, variola major, variola minor, spirillum minus infection, *sporothrix schenckii* infection, *staphylococcus aureus* infection, strongyloidiasis, *treponema* palladium infection, thalassemia, thromobophilia, relapsing fever, *toxocara* infection, verruga peruana, west nile infections, whoppint cough, Whitmore's disease, seontropic murine leukemia virus-related virus infection, yellow fever, and yersiniosis.

At high frequencies, identification of cell infection based on the measured degree of stretch substantially decreases. While not wanting to be limited by theory, it is believed that classification of cell behavior based on elasticity alone neglects the viscoelastic nature of the cell. Accordingly, elastic measurements are typically, but not necessary, confined within the near equilibrium processes temporal limits.

Infection commonly stiffens the cell cytoskeleton. The stiffen cell cytoskeleton generally affects cell elasticity and can significantly alter the cell's viscous properties. For example, when subject to an oscillating external loading force, the cell's viscoelastic properties follows the external loading force with a delayed mechanical response to the external loading (FIG. 1). The delayed mechanical response is typically observed as a phase lag (see FIG. 1). The phase lags for healthy and infected cells differ.

Figure 5:
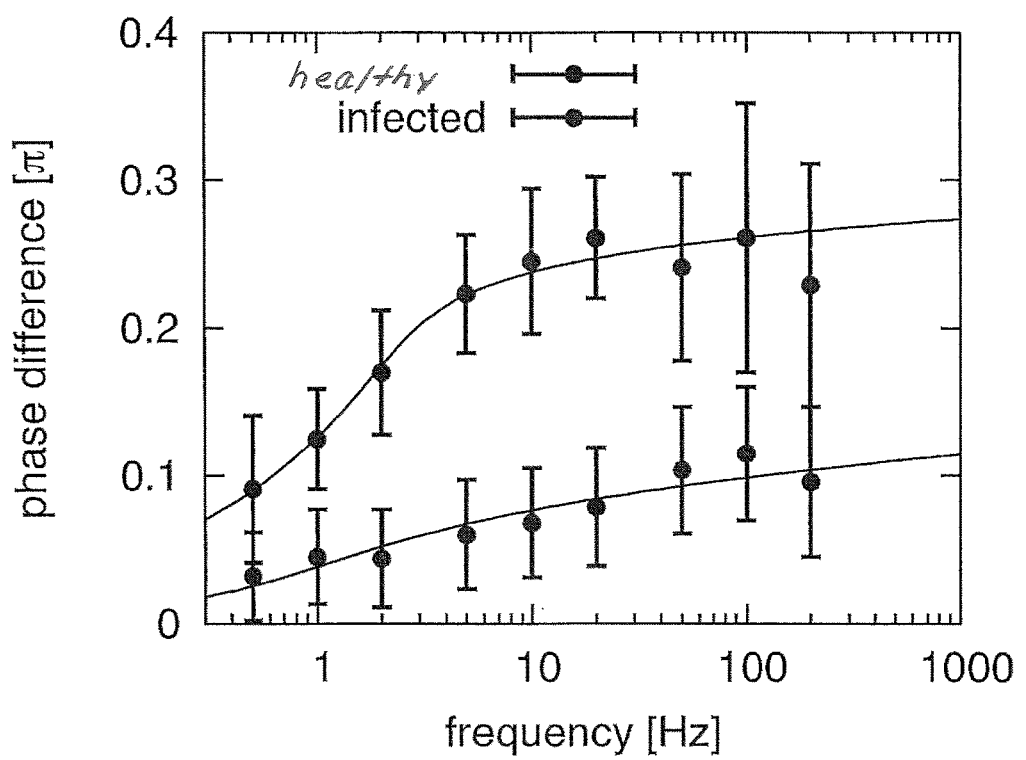
FIG. 5 depicts measured phase differences between an applied modulated force and a cell response for healthy and infected cells.

FIG. 5 shows the measured phase shift $\delta$ between stimulus and response for healthy and infected cell populations as the modulation frequency is varied. A steep increase in the phase shift $\delta$ difference was observed for healthy cells at higher modulation frequencies. The phase shift $\delta$ reached a plateau at about $\delta=\pi/4$ for healthy cells. Infected cells had a distinctly reduced phase shift $\delta$ lag and reduced lag and a maximum of $\delta=\pi/8$. Compared to healthy cells, the behavior of infected cells can be described as more solid-like with a more immediate response to external loading. This difference in the reaction time of healthy and infected populations explains the observed crossover in the frequency-dependent stretching in FIG. 4. The stiffer infected cells are less affected by increasing modulation frequencies than the healthy cells. The stiffen-cellular cytoskeleton of the infected cell affected the erythrocyte elasticity and significantly altered viscous properties (FIG. 5).

Furthermore, FIG. 5 shows the differences in the measured phase shift $\delta$ between the applied force and/or stress to the cell and the cellular response (strain) for healthy 501 and infected 503 cells over the modulated frequency range of between about 0.1 to about 1,000 Hz. The measured phase shift $\delta$ for infected cells exhibits a slight increase in phase shift $\delta$ over the modulation frequency range. This is in contrast to healthy cells, the measured phase shift $\delta$ for healthy cells exhibits a increase in the measured phase shift $\delta$ at modulation frequencies of less than about 5 Hz and a measured phase shift $\delta$ of about 2.5 times that of the infected cells over the frequency range of between about 5 to about 1,000 Hz.

Figure 6:
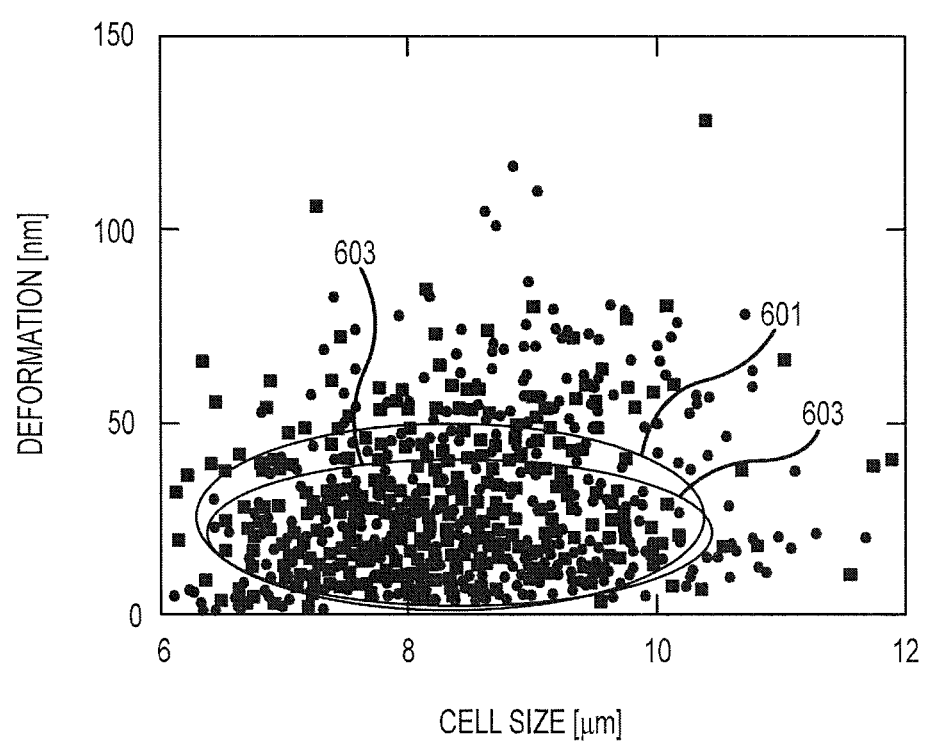
FIG. 6 depicts a scatter plot of measured cell deformations for healthy and infected cells.
Figure 7:
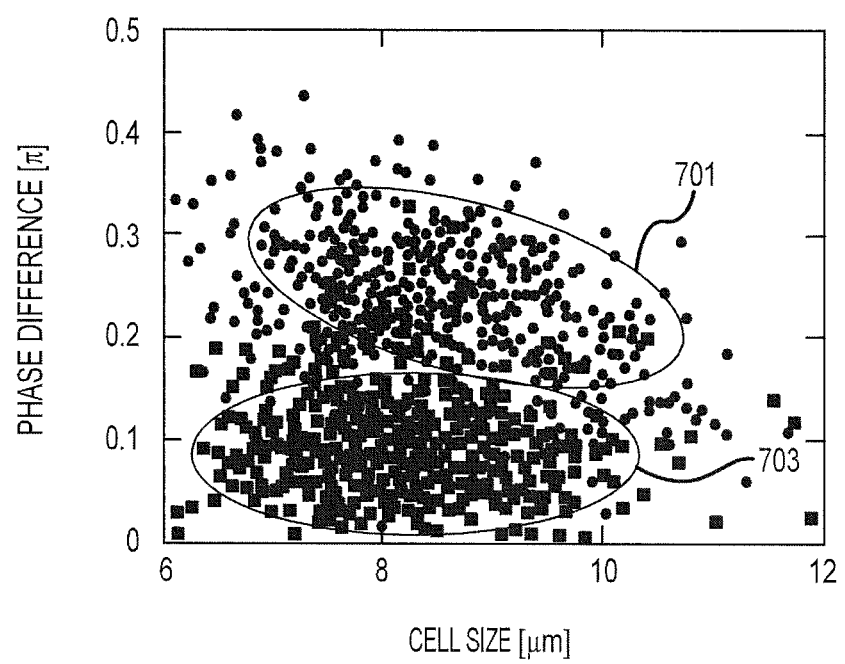
FIG. 7 depicts a scatter plot of measured phase differences between an applied modulated force and the cell response for healthy and infected cells.

Measuring the viscous contribution to the stretching behavior provides an additional cell mechanical biomarker to characterize and classify cellular systems at much faster timescales than the near-equilibrium elasticity measurements. This is demonstrated by the non-equilibrium stretching deformation and phase shift δ distribution differences at frequencies of about 5 Hz or greater (see FIGS. 6 and 7). FIG. 6 shows a significant overlap of domains 601 and 603 in the elastic response for healthy (depicted by circles) and infected (depicted by squares) cells, respectively. However, clear distinct healthy (healthy) 701 and infected 703 domains are apparent in the inelastic response of the cells respectively (FIG. 7). The mechanical behavior differences of healthy and infected cells at higher modulation frequencies enable reliable cell classification beyond equilibrium timescales, such as timescales where purely elasticity-based mechanical analysis methods typically fail.

The relevance of these findings is not limited to dynamic stretching with periodic loading but also impacts static cell deformation such as stretch-and-release measurements. Cell viscosity also affects cell relaxation dynamics (or so-called creep), a delayed material response to external loading and is seen not only in the phase-shifted oscillating stretching but also in the characteristic cell relaxation dynamics. A measure of these time-dependent dynamic viscoelastic properties G* can be seen, in addition to phase-shifted oscillating stretching, in viscoelastic properties such as delayed response (strain) to applied force and/or stress, commonly referred to as creep, or static viscoelastic properties associated with "stretch-and-release" determination. In other words, the dynamic viscoelastic properties G* of healthy and infected cells can be understood in terms of one or both of the storage modulus G' and loss modulus G" of the healthy and/or infected cells. The storage modulus G' can be expressed as:

$$G'=(\alpha/\epsilon)\cos(\delta) \quad (2)$$

and the loss modulus G" can be expressed as:

$$G''=(\alpha/\epsilon)\sin(\delta) \quad (3)$$

where α is the applied force and/or stress, ε is the resulting strain, and δ is the phase sift between the applied force and/or stress and the resulting strain.

Figure 8:
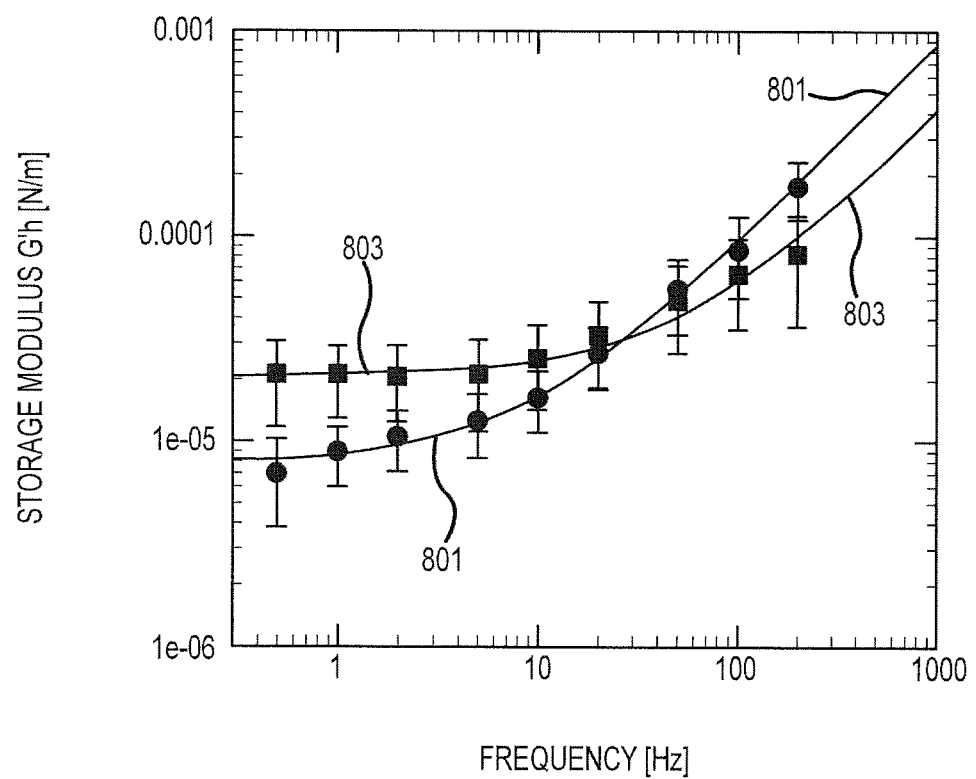
FIG. 8 depicts a plot of storage modulus versus applied frequency for healthy and infected cells.
Figure 9:
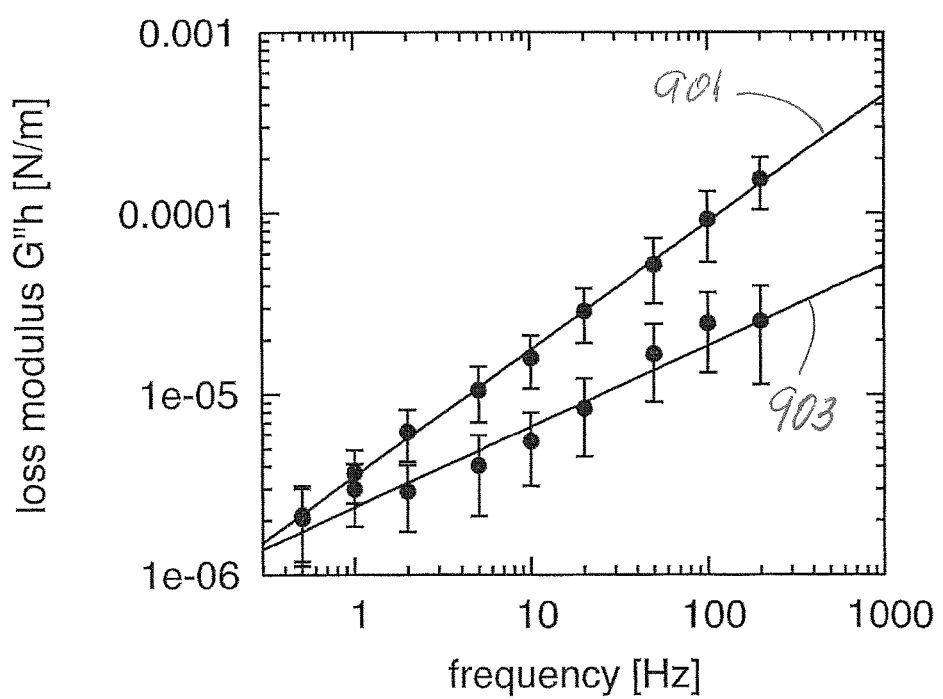
FIG. 9 depicts a plot of loss modulus versus applied frequency for healthy and infected cells.

FIGS. 8 and 9 show the frequency dependence of the measured storage modulus G' (FIG. 8) and loss modulus G" (FIG. 9) for healthy (801 and 901, respectively) and infected (803 and 903, respectively) cell populations are shown over a modulated frequency range between 0.1 to 1,000 Hz, where a was determined using a simulation and ε and δ were determined from the experimental data of FIGS. 4 and 5. Error bars were derived from the standard deviations of the deformability and phase difference distributions, providing a measure for the spread of population-based experiments.

The moduli were calculated using a ray-tracing simulation to estimate the inner-membrane stress α generated by the applied optical forces. The laser is modeled as an array of individual light rays using experimentally measured geometrical parameters of the Gaussian beam profile and a model cell placed in the laser focus that refracts incoming light according to Snell's law. The gain of momentum and the change of light direction are balanced by an opposing momentum transferred to the cell membrane, inducing local deformation. The distribution of optical forces over the cell surface is calculated and the generated inner-membrane stress α responsible for cell elongation along the inner trap axis determined.

Healthy cells had a near equilibrium storage modulus (FIG. 8, red blood cells) G'h of about $8.0 \cdot 10^{-6}$ N/m (line 801 at about 0.1 Hz), where h is a normalization by the cell membrane thickness. The storage modulus value agreed well with results of conventional equilibrium, low frequency techniques. Infected cells had significant cell stiffness with an increased equilibrium shear modulus (line 803 at about 0.1 Hz, malaria-infected red blood cells) of G'h of about $21 \times 1010^{-6}$ N/m.

At frequencies greater than about 0.1 Hz, the storage moduli of the healthy and infected cells converge (lines 801 and 803). Accordingly, the storage modulus is generally a less preferred mechanical-property for discriminating healthy and infected cells at high frequency timescales.

The near equilibrium loss moduli of healthy and infected cells converge at low frequencies (FIG. 9, red blood cells) for near-equilibrium cell stretching. Over the frequency range of between 0.1 to about 1,000 Hz, the loss moduli G" of healthy and infected cells follow a power law, $c\omega^\beta$, where c is constant, ω the modulation frequency, and β a power coefficient which differs substantially for healthy and infected cells. The power law relationship provides for a ten-fold difference in the loss moduli of healthy and infected cells at about 200 Hz and at high frequencies a clear signal for infection.

The power coefficient β for healthy cells was about 0.70±0.01 (red blood cells). The power coefficient for infected cells was substantially less, 0.45±0.04 (malaria-infected red blood cells). The loss modulus for an infected cell at about 200 Hz was about G'h=$2 \cdot 10^{-5}$ N/m (line 901). A healthy cell had a loss modulus at about 200 Hz of about a factor of ten times greater than that of the infected red blood cell, with a G'h of about $2 \cdot 10^{-4}$ N/m (line 903).

The power law relationship of the loss modulus and substantial difference in the power coefficient for healthy and infected cells provides for a clear distinction of healthy and infected cells high frequencies. Furthermore, the distinction of healthy and infected cells can be achieved at shorter timescales where cells are typically unable to equilibrate. Moreover, the elasticity of the cellular cytoskeleton and viscous dissipation can be quickly and easily determined.

Figure 10A:
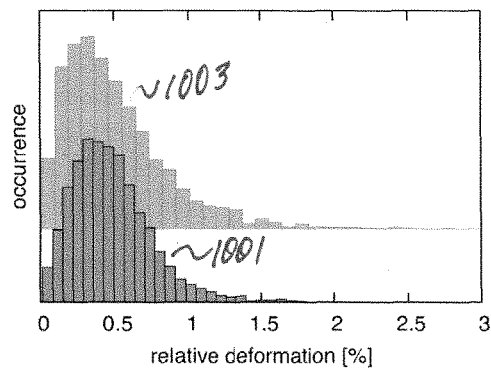
FIG. 10A depicts distributions of recorded deformations measured at frequencies of about 10 Hz at rates of more than about 20 cells/s of infected and healthy populations of about 3000 cells.
Figure 10B:
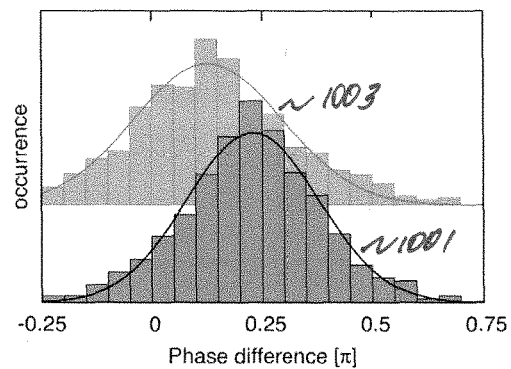
FIG. 10B depicts distributions of recorded phase shifts measured at frequencies of about 10 Hz at rates of more than about 20 cells/s of infected and healthy populations of about 3000 cells.

The viscoelastic behavior of healthy and infected cell populations were investigated a flowing environment. Throughput was determined using dense cell solutions flushed through the microfluidic channel between about 500 to about 750 mm/s. To facilitate detection, laser intensity was increased to about 405 mW at 100 Hz. FIGS. 10A and 10B show the measured distributions of relative cell deformation and phase shift for a population of about 3000 cells comprising a mixture of infected 1003 and healthy 1001 cells recorded at a rate of more than about 20 cells/s. The detected spread of the data is broader than the static measurements due to the reduced timescales in the high-throughput measurements with standard deviations of 0.15π for healthy cells (red blood cells) and 0:17π for infected cells (malaria-infected cells). The center values of the distributions at δ 0.23π for healthy cells and δ0.13π for infected cells. These values agree well with static values determined in the absence of flow. A two-sample t-test was performed for these distributions with the null hypothesis tested at a significance level of 0.1%. Throughputs were limited primarily by the speed of imaging and detection. Significantly faster rates are expected by employing higher modulation frequencies with more rapid measurement methods.

EXAMPLES

Modulated Linear Optical Traps

Linear optical traps were created using an astigmatic beam of a laser diode (JDSU, 2495-Y-5.0 W, 810 nm, Milpitas, Calif.) with an emitter of size 1 μm×100 μm using a 20× objective (Zeiss, APlan 20×/0.45, Jena, Germany).

The beam was reflected at a dichroic mirror and refocused by a 40× microscope objective (Olympus, UPlanApo 40×/0.85, Olympus, Pa.) into a sample plane, generating a linear optical trap of dimension 0.94 μm by 40 μm. Beam properties in the focus were measured employing a razor blade method for beam characterization and modeling. A 12 W white light LED (430 Lumen Cool-White, Cree, North Carolina) employing condenser lenses and a 10 microscope objective (10/0.25, Edmund Optics, Barrington, N.J.) was used for illumination. The sample plane was imaged by the same objective focusing the laser to a digital camera through the dichroic mirror. A high-speed CMOS camera system (Silicon Video 643 M, EPIX, Buffalo Grove, Ill.) was employed to record the region of interest (100 by 100 pixels, 29 μm by 29 μm) at 1,000 frames/second.

The employed linear traps constrict the motion of captured microscopic objects in one dimension while allowing translation in the other. In general, when focused laser light hits a surface of higher refractive index than the surrounding medium, momentum is transferred, generating restoring forces directed toward the focus center. In trapping soft objects such as biological cells, however, this transfer of momentum leads to additional local stresses within the membrane surface. The asymmetric distribution of laser light inherent to the linear traps generates anisotropic optical forces and induces axial, antipodal stretching forces and cell elongation along the trap long 105 axis (FIG. 2). For static measurements, moderate laser powers of about 95 mW were distributed over the linear trap 100, limiting the exposure per cell to about 20 mW and substantially preventing radiation damage. To ensure viability, long-term measurements were performed with continuous, repeated cell stretching over several minutes at different frequencies with no observable changes in elastic behavior.

Microfluidic Channels

Experiments were performed in in straight microfluidic channels of dimensions 2 cm×1000 μm×10 μm, fabricated by common soft lithography methods. In this, a spin-coated layer of KMPR 1010 (Microchem, Newton, Mass.) was exposed through a mask by ultraviolet light, generating a template of the desired channel structure. Polydimethylsiloxane (PDMS, Dow Corning, Midland, Michiana) was poured over this template and polymerized, leaving the imprints of the channel relief in the cured polymer. Cured PDMS was then plasma-bonded to glass coverslips, sealing the channel structures. Inlets and outlets were punched through the PDMS layer and tubing attached to deliver blood sample solutions and control flow rates. Channels were rinsed with buffer solution ~3 h before the experiments to allow the adhesion of BSA to channel walls to prevent cell adhesion.

Frequency Sweep Measurements

To obtain a comprehensive picture of the complex mechanical characteristics of probed cells, their viscoelastic behavior was investigated when exposed to oscillating optical force loading in the absence of external flow. Membrane viscosity is responsible for the characteristic retardation of the cell response; therefore, a phase shift between stimulus and response is expected (FIG. 1) depending on the frequency of oscillation. The laser intensity was modulated using an external frequency generator coupled to the laser diode power source and subjected cells to oscillating optical stretching forces while recording their time-dependent response to the external loading. Employed frequencies ω ranged from 0.5 Hz, where full equilibrium cell stretching is achieved, to 200 Hz where it is not achieved. The upper limit is defined by the speed of the detection method, a high-speed camera running at 1000 fps. To detect the phase shift between applied force and cell response, the original modulation signal of the frequency generator was read using a sound card (SB0570L4, Creative Labs, Milpitas, Calif.) and encoded in the brightness value of a corner pixel within recorded videos.

Image Detection and Data Analysis

Analyzing the videos of cells stretched within the linear optical trap, the brightness of the pixel encoding the original modulation signal was read and its time variation fit by a sine function to capture any deviation from frequency generator predefined values. The cell response to the modulated stimulus was analyzed using custom image detection software.

Video quality was improved by subtracting the previously recorded fixed-pattern noise, resulting in background corrected images. Each frame was converted into a binary black and white image using a preset threshold value, enabling the detection of cell contours. Ellipses were fit to the cell contours, obtaining sub-pixel resolution of the cell dimensions and other parameters from the orientation and length of long and short axes of the ellipse.

Figure 11:
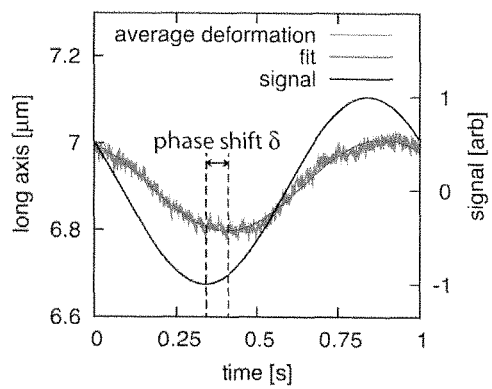
FIG. 11 depicts a mean period of oscillation from averaging data points with substantially identical phase shifts.
Figure 12:
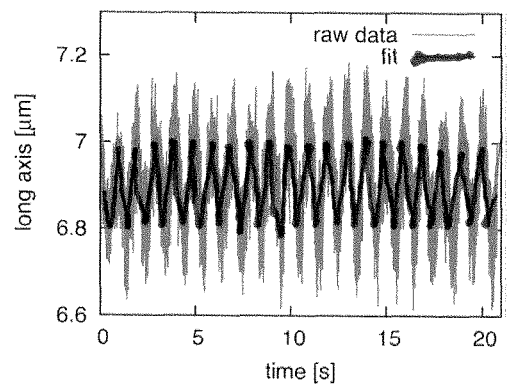
FIG. 12 depicts raw data and fit function obtained from the mean cell deformation.

Employing this method to measure the dimensions of rigid colloidal beads of well-known size indicated an inherent random noise with magnitudes of the order of about 20 nm associated with the applied algorithms. To detect even smaller amplitudes of cell stretch, each video covered several 10 to 100 oscillations, allowing averaging over multiple data points with an identical phase of modulation, gaining one mean period of oscillation with significantly reduced noise, as shown in FIG. 11 for a modulation frequency of 1 Hz. A sine function is fit to this averaged period to determine amplitude and phase of the cell response to the modulated external force. FIG. 12 compares this fit to the mean deformation cycle and the raw data acquired in about 20 s, illustrating the reduction of noise due to the applied averaging algorithm. Even higher sensitivity can be achieved by increasing the number of periods for averaging. At high modulation frequencies with averaging over about several 100 deformation cycles amplitudes down to about 2 nm were resolved. The accuracy of the detection of such small deformations is supported by the consistency of the measured phase of the cell response with respect to the applied external stimulus as a control parameter.

Applying this method to measure the dimensions of rigid colloidal beads of well-known size indicated an inherent noise of order about 20 nm. To detect even smaller amplitudes of cell stretch, each video covered several 10 to 100 oscillations. Data points with identical phase of modulation were averaged. Averaging significantly reduced noise.

High-Throughput Measurements

Based on the insights gained from the measured viscoelastic properties of cells in static systems over a frequency range of about three orders of magnitude, cell behavior in flowing environments was investigated. Samples containing about 60 ml blood per ml BSA solution were flushed through the microfluidic channels at about 500 to about 750 m/s driven by gravity. To minimize the probing time of an individual cell while acquiring sufficient video data per period, the optical trap was modulated at about 100 Hz. To facilitate detection, laser intensity distributed over the entire trap was increased to about 405 mW resulting in a larger cell deformation with less than about 80 mW exposure per cell. With two full periods of oscillation, the time of an individual cell through the linear optical trap was about 20 ms or greater, well below typical relaxation timescales. Long-term studies to test the viability of cells at these increased laser intensities showed variations in cell deformability and appearance only after about 30 to about 60 s or more, orders of magnitude above actual exposure times used in the measurements.

Blood Samples

Blood samples were prepared by diluting 1.5 μl of fresh blood from anonymous donors in 500 μl a 300 mOsm buffer solution, consisting of phosphate buffered saline solution, 1.47% sodium citrate, and 0.20% bovine serum albumin. Human erythrocytes were obtained from Interstate Blood Bank (Memphis, Tenn.) and used for in vitro *Plasmodium falciparum* cultivation. Trophozoite stage infected cells were enriched to a greater than about 95% parasitemia by Percoll-sorbitol density gradient centrifugation and then frozen in glycerolyte 57 (Baxter Fenwal, Lake Zurich, Ill.). The frozen cells were thawed using stepwise dilutions with hypertonic saline to reduce hemolysis. To exclude artifacts associated with freezing and subsequent thawing, control measurements on frozen healthy erythrocytes were preformed and shown to have no deviation from freshly drawn blood.

A number of variations and modifications of the invention can be used. It would be possible to provide for some features of the invention without providing others.

The present invention, in various embodiments, configurations, or aspects, includes components, methods, processes, systems and/or apparatus substantially as depicted and described herein, including various embodiments, configurations, aspects, sub-combinations, and subsets thereof. Those of skill in the art will understand how to make and use the present invention after understanding the present disclosure. The present invention, in various embodiments, configurations, and aspects, includes providing devices and processes in the absence of items not depicted and/or described herein or in various embodiments, configurations, or aspects hereof, including in the absence of such items as may have been used in previous devices or processes, e.g., for improving performance, achieving ease and/or reducing cost of implementation.

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments, configurations, or aspects for the purpose of streamlining the disclosure. The features of the embodiments, configurations, or aspects of the invention may be combined in alternate embodiments, configurations, or aspects other than those discussed above. This method of disclosure is not to be interpreted as reflecting an intention that the claimed invention requires more features than are expressly recited in each claim. Rather, as the following claims reflect, inventive aspects lie in less than all features of a single foregoing disclosed embodiment, configuration, or aspect. Thus, the following claims are hereby incorporated into this Detailed Description, with each claim standing on its own as a separate preferred embodiment of the invention.

Moreover, though the description of the invention has included description of one or more embodiments, configurations, or aspects and certain variations and modifications, other variations, combinations, and modifications are within the scope of the invention, e.g., as may be within the skill and knowledge of those in the art, after understanding the present disclosure. It is intended to obtain rights which include alternative embodiments, configurations, or aspects to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method for assessing relative cellular health with at least one viscoelastic property, comprising:
generating with a modulated laser beam a substantially linear optical trap, wherein the substantially linear optical trap has a longitudinal optical trap axis;
aligning twenty or more cells in the linear optical trap;
flowing the twenty or more cells in the linear optical trap along the longitudinal optical trap axis;
applying a modulated stress generated by the modulated laser beam to the aligned twenty or more cells to strain the twenty or more cells; and
measuring a storage modulus and a loss modulus for the twenty or more cells from a lag between the applying of the modulated stress and the resulting strain on the twenty or more cells along the longitudinal optical trap axis.

2. The method of claim 1, wherein the modulated laser beam has a frequency between about 0.1 to about 1000 Hz, and wherein the modulated stress exposes each cell of the twenty or more cells to no more than about 20 mW of laser power.

3. The method of claim 1, wherein the optical trap has a cross-sectional shape of at least one of a channel, a groove, a U-shape and an inverted arch.

4. The method of claim 1, wherein the optical trap further has a transverse optical trap axis and wherein transverse optical trap axis constrains movement of the twenty or more cells more than the longitudinal optical trap axis.

5. The method of claim 1, further comprising comparing the strain measured to a database of healthy and infected cellular strains to determine the relative health of the twenty or more cells.

6. A method of assessing cellular viscoelastic properties, comprising:
flowing within a linear optical trap formed by a modulated laser beam one or more cells, wherein the optical trap has a substantially longitudinal optical trap axis and a transverse optical trap axis, and wherein the one or more cells have greater mobility along the longitudinal optical trap axis than the transverse optical trap axis;
applying a modulated force to the one or more cells by modulating the laser beam, and wherein the modulated force stretches the one or more cells along the longitudinal optical trap axis; and
measuring storage and loss moduli from a lag between the applying of the modulated force to the one or more cells and the stretch of the one or more cells.

7. The method of claim 6, wherein the modulated laser beam is an astigmatic laser beam.

8. The method of claim 6, wherein the flowing step further comprises flowing the one or more cells along the longitudinal optical axis at a flow rate of between about 500 to about 750 μm/s.

9. The method of claim 6, wherein the measuring of the lag further comprises measuring the strain on the one or more cells along the longitudinal optical trap axis.

10. The method of claim 6, wherein the laser beam has a power between about 350 to about 450 mW.

11. The method of claim 6, wherein the modulated force applied to the one or more cells has a frequency between about 0.1 to about 1,000 Hz.

12. The method of claim 11, wherein the modulated force applied to the one or more cells is for a period of less than about 10 seconds for frequencies of no more than about 500 Hz.

13. The method of claim 12, wherein the laser beam exposes each of the one or more cells to no more than about 20 mW of laser power.

14. The method of claim 11, wherein the modulated force applied to the one or more cells is for a period of less than about 30 seconds for frequencies of about 500 Hz or more.

15. The method of claim 14, wherein the laser beam exposes each of the one or more cells to no more than about 20 mW of laser power.

16. The method of claim 6, wherein the one or more cells comprise at least one of:
   healthy red blood cell(s);
   infected red cell(s); or
   a mixture of healthy and infected red blood cells.

17. A method of assessing viscoelastic properties of red blood cells, comprising:
   flowing the red blood cells through a substantially linear optical trap generated by a modulated laser beam, wherein the substantially linear optical trap has a longitudinal optical trap axis and a transverse optical trap axis, and wherein the red blood cells have greater mobility along the longitudinal optical trap axis than the transverse optical trap axis;
   applying, by the modulated laser beam, a modulated force having a frequency between about 0.1 to about 1,000 Hz to the red blood cells, wherein the modulated force stretches the red blood cells along the longitudinal optical trap axis; and
   measuring dynamic and/or complex elastic moduli from a lag between the applying of the modulated force to the red blood cells and the stretch of the red blood cells.

18. The method of claim 17, wherein the laser beam exposes the cells to no more than about 20 mW of laser power.

19. The method of claim 17, wherein the modulated force is applied for less than about 10 seconds.

20. The method of claim 17, wherein the red blood cells comprise at least one of:
   healthy red blood cell(s);
   infected red cells(s); or
   a mixture of healthy and infected red blood cells.

* * * * *

UNITED STATES PATENT AND TRADEMARK OFFICE
CERTIFICATE OF CORRECTION

PATENT NO. : 9,885,644 B2
APPLICATION NO. : 14/307269
DATED : February 6, 2018
INVENTOR(S) : Tobias Sawetzki et al.

Page 1 of 1

It is certified that error appears in the above-identified patent and that said Letters Patent is hereby corrected as shown below:

In the Specification

Column 1, Lines 30-36 delete:
"STATEMENT REGARDING FEDERALLY SPONSORED RESEARCH OR DEVELOPMENT
This invention was supported in part with funding provided by National Science Foundation Grant No. DBI-0852868 and National Institutes of Health Grant No. IR0I AI079347."

And insert:
--GOVERNMENT LICENSE RIGHTS
This invention was made with government support under grant AI079347 awarded by National Institutes of Health. The government has certain rights in the invention.--

Signed and Sealed this
Ninth Day of October, 2018

Andrei Iancu
*Director of the United States Patent and Trademark Office*